United States Patent [19]

Anderson

[11] Patent Number: 5,000,755
[45] Date of Patent: Mar. 19, 1991

[54] NITROSO COMPOUNDS AS DIRECT DYES

[75] Inventor: James S. Anderson, Danbury, Conn.

[73] Assignee: Clairol Incorporated, New York, N.Y.

[21] Appl. No.: 554,648

[22] Filed: Jul. 19, 1990

[51] Int. Cl.$^5$ ............................................. A61K 7/13
[52] U.S. Cl. ......................................... 8/405; 8/414; 8/428; 8/429
[58] Field of Search .................... 8/414, 428, 429, 405

[56] References Cited

U.S. PATENT DOCUMENTS 4,473,374  9/1984  Bugaut et al. ............................ 8/405

Primary Examiner—Paul Lieberman
Assistant Examiner—William S. Parks
Attorney, Agent, or Firm—Morton S. Simon

[57] ABSTRACT 4-nitroso anilines and cosmetically acceptable salts thereof are employed as direct dyes. Compositions for dyeing keratin fibers and containing said 4-nitroso anilines and an alkalizing agent are also disclosed.

4 Claims, No Drawings

NITROSO COMPOUNDS AS DIRECT DYES

BACKGROUND OF INVENTION

1. Field of Invention

The present invention relates to 4-nitroso anilines of the formula I

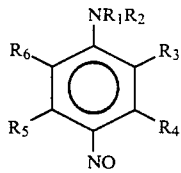

wherein $R_1$ and $R_2$ are the same or different, and are H, $C_1$-$C_6$ alkyl, $C_1$-$C_6$ hydroxyalkyl or polyhydroxyalkyl, $C_1$-$C_6$ alkoxyalkyl or polyalkoxyalkyl, $C_1$-$C_6$ amino alkyl, $C_1$-$C_6$ dialkylaminoalkyl, or $R_1$ and $R_2$ taken together with the nitrogen atom to which they are attached may be a heterocyclic ring selected from the group consisting of morpholino, pyrrolidino, piperidino and piperazino; $R_3$, $R_4$, $R_5$, and $R_6$ can be the same or different, and are H, $C_1$-$C_6$ alkyl, $C_1$-$C_6$ hydroxyalkyl or polyhydroxyalkyl, hydroxy, $C_1$-$C_6$ alkoxy, $C_1$-$C_6$ hydroxyalkoxy or polyhydroxyalkoxy, or halogen; and cosmetically acceptable salts thereof. The instant invention also relates to the use of the compounds of formula I as direct dyes and to compositions for dyeing keratin fibers containing compounds of formula I.

2. Description of the Prior Art 4-nitroso anilines are known in the art. U.S. Pat. Nos. 4084052 and 4023926 disclose examples of such compounds as reactants in processes for producing other compounds of interest. In the reactions disclosed the nitroso group is lost.

U.S. Pat. No. 3970423 discloses solutions of 4-nitroso-N,N-disubstituted anilines in isopropanol. The disclosed 4-nitroso-N,N-disubstituted anilines function as intermediates which undergo further reaction to produce substituted p-phenylenediamines.

The Colour Index discloses several nitrosophenols as mordant dyes which form color upon complexation with a metal. The compounds disclosed are not anilines and merely serve as intermediates to dyes.

British patent 2141437 discloses nitroso compounds for synthesis of indoaniline and indophenol compounds.

Color Chemistry—Synthesis, Properties and Applications of Organic Dyes and Pigments—Zollinger VCH, 1987, Chapter 6—Nitro and Nitroso Dyes, pp 83-84, discloses hydroxy nitroso compounds which are used exclusively as metal complex dyes.

Although there is a considerable amount of prior art relative to the 4-nitroso anilines, we are unaware of any prior art appreciation of the use of such compounds as direct hair dyes.

SUMMARY OF THE INVENTION

We have found that certain 4-nitroso anilines, as defined below, surprisingly and unexpectedly dye hair bright colors that are shampoo and light stable.

The 4-nitroso anilines of the present invention conform to the formula I

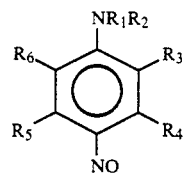

wherein $R_1$ and $R_2$ are the same or different, and are H, $C_1$-$C_6$ alkyl, $C_1$-$C_6$ hydroxyalkyl or polyhydroxyalkyl, $C_1$-$C_6$ alkoxyalkyl or polyalkoxyalkyl, $C_1$-$C_6$ amino alkyl, $C_1$-$C_6$ dialkylaminoalkyl, or $R_1$ and $R_2$ taken together with the nitrogen atom to which they are attached may be a heterocyclic ring selected from the group consisting of morpholino, pyrrolidino, piperidino and piperazino; $R_3$, $R_4$, $R_5$, and $R_6$ can be the same or different, and are H, $C_1$-$C_6$ alkyl, $C_1$-$C_6$ hydroxyalkyl or polyhydroxyalkyl, hydroxy, $C_1$-$C_6$ alkoxy, $C_1$-$C_6$ hydroxyalkoxy or polyhydroxyalkoxy, or halogen; and cosmetically acceptable salts thereof.

Preferred compounds of formula I include those compounds wherein $R_1$ and $R_2$ are the same and are $C_1$-$C_6$ alkyl, $C_1$-$C_6$ hydroxyalkyl or $C_1$-$C_6$ alkoxyalkyl.

More preferred compounds of the formula I include those compounds wherein $R_1$ and $R_2$ are the same and are $C_1$-$C_6$ alky, $C_1$-$C_6$ hydroxyalkyl or $C_1$-$C_6$ alkoxyalkyl and $R_3$, $R_4$, $R_5$, and $R_6$ are, independently, H, $C_1$-$C_6$ alkyl, or hydroxy.

Still more preferred compounds of the formula I are those wherein $R_1$ and $R_2$ are the same and are $C_1$-$C_6$ alkyl, $C_1$-$C_6$ hydroxyalkyl or $C_1$-$C_6$ alkoxyalkyl; $R_3$, $R_5$, and $R_6$ are hydrogen; and $R_4$ is H, $C_1$-$C_6$ alkyl, or hydroxy.

Most preferred are compounds of the of the formula I wherein $R_1$ and $R_2$ are the same and are $C_2$-$C_4$ alkyl, hydroxyethyl or ethoxyethyl; $R_3$, $R_5$, and $R_6$ are hydrogen; and $R_4$ is hydrogen, methyl or hydroxy.

4-nitrosoanilines of formula I have a number of advantages. They are intensely colored ($\epsilon \approx 10^4$). They are equal in intensity to 4-nitroanilines, a class whose extinction coefficients are among the highest of the nitro dyes. Moreover, they are more light stable than the 4-nitroanilines. This is indeed surprising and unexpected since the nitro compounds fade off-shade upon exposure to light and they are close analogues of the nitroso compounds. Thus, prior to our discovery, one skilled in the art would have expected that 4-nitroso anilines of formula I would exhibit similar light instability.

4-nitroanilines which, as stated above, are close analogies of the nitroso compounds have very low aqueous solubility. Contrary to expectations the nitroso compounds of formula I are surprisingly very water soluble. This property allows higher concentrations of the nitroso dyes of formula I in aqueous-based dyeing systems than are attainable with the nitro dyes.

To illustrate the intensity of the 4-nitroso anilines of formula I, λ max and logε were determined in 95% ethanol for representative compounds of formula I. The results are set forth in the following Table I.

It should be noted that, unless indicated to the contrary, percent, as used herein, means by weight based on the total weight of the composition.

TABLE I

| Compound No. | Nitroso aniline of formula I | | | λmax | log ξ |
|---|---|---|---|---|---|
| | R$_1$ & R$_2$ | R$_4$ | R$_3$, R$_5$, & R$_6$ | | |
| 1 | —CH$_2$CH$_2$OH | H | H | 428 nm | 4.38 |
| 2 | —CH$_2$CH$_3$ | H | H | 429 nm | 4.53 |
| 3 | —CH$_2$CH$_2$OCH$_2$CH$_3$ | H | H | 416 nm | 4.31 |
| 4 | —CH$_2$CH$_2$CH$_2$CH$_3$ | H | H | 430 nm | 4.09 |
| 5 | —CH$_2$CH$_2$OH | CH$_3$ | H | 430 nm | 4.63 |
| 6 | —CH$_2$CH$_3$ | OH | H | 401 nm | 4.08 |
| | | | H | 335 nm | 4.10 |

EXAMPLE (A) 0.4% of Compound 1 of Table I (4-nitrosophenyl) diethanolamine was dissolved in a dye base (containing thickener, preservative, surfactants, solvents, fragrance, alkalizing agent and water). Blended grey hair was dyed with the resultant composition for 30 minutes at ambient temperature then rinsed and dried. Color quantification and light fastness were ascertained by the method of Lim and Anderson reported in U.S. Pat. No. 4,799,934, issued Jan. 24, 1989 (see col. 11). Total color change after 10 hours exposure to light in a Fad-o-meter, defined as $$\sqrt{(\Delta L)^2 + (\Delta a)^2 + (\Delta b)^2}$$ , was 3.4.

(B) For comparative purposes, 0.4% of (4-nitrophenyl) diethanolamine (the corresponding nitroaniline analogue of the dye employed in part (A) above) was dissolved in the same dye base as was employed in part (A) above. Blended grey hair was dyed with the resultant composition for 30 minutes at ambient temperature then rinsed and dried. Color quantification and light fastness were determined as described in part (A) above. Total color change after 10 hours exposure to light in a Fad-o-meter, defined as $$\sqrt{(\Delta L)^2 + (\Delta a)^2 + (\Delta b)^2}$$ , was 6.2.

A comparison of light stability results of parts (A) and (B) of this example demonstrates the unexpected and surprising substantial increase in light stability of the nitrosoaniline compounds of the present invention over their nitroaniline analogues.

(C) Hair dyed in accordance with part (A) of this example and hair dyed in accordance with part (B) of this example were subjected to six hand shampoos. Stability of the nitroso-aniline compound 1 of Table I to six hand shampoos was essentially equivalent to that of its nitroaniline analogue (4-nitrophenyl diethanolamine) ($\Delta L$ for the nitro compound is 0.6; $\Delta L$ for the nitroso compound is 0.7).

(D) Each of nitrosoaniline Compounds 2, 3, 4, 5 and 6 of Table I when evaluated as described in part (A) of this example demonstrates unexpected superior light stability as compared to its respective nitroaniline analogue.

In addition to the use of 4-nitroso anilines of formula I as direct hair dyes, the present invention provides novel hair compositions containing a 4-nitroso aniline of the aforementioned formula I, or a cosmetically acceptable salt thereof, in an amount sufficient to function as a direct dye on keratin fibers, and a cosmetically acceptable direct dye base containing an alkalizing agent in an amount sufficient to facilitate penetration of the nitroso aniline, or cosmetically acceptable salt thereof, into the keratin fibers to directly dye same.

Preferably, the nitrosoaniline compound of the present invention is present in the composition in an amount, of about 0.01% to about 5.0%.

More preferably, such amount is from about 0.05% to about 2.5%.

Most preferably, it is from about 0.1% to about 2%.

The alkalizing agent is preferably selected from the group consisting of ammonia; sodium, potassium, or ammonium carbonate; sodium or potassium hydroxide; monoalkanolamines, e.g. monoethanolamine, N-methyl,-ethyl, or-propyl ethanolamine, 2-amino-2-methylpropanol, 1-amino-2-propanol, 2-amino-1-propanol, N,N-dialkylaminoethanol and N,N-dialkylaminopropanol; alkylamines, trialkyl or trialkanolamines, e.g. triethanolamine; dialkyl and dialkanolamines, e.g. diethanolamine; amino alkyldiols, e.g. 2-amino-2-ethyl-1,3-propanediol; and amino alkyltriols, e.g. 2-amino-2-hydroxymethyl-1,3-propanediol.

More preferably, the alkalizing agent is selected from the group consisting of monoalkanolamines, e.g. monoethanolamine N-methyl,-ethyl, or-propyl ethanolamine, 2-amino-2-methylpropanol, 1-amino-2-propanol, 2-amino-1-propanol, N,N-dialkylaminoethanol and N,N-dialkylaminopropanol; trialkyl or trialkanolamines, e.g. triethanolamine; amino alkyldiols, e.g. 2-amino-2-ethyl-1,3-propanediol; and aminoalkyltriols, e.g. 2-amino-2-hydroxymethyl-1,3-propanediol.

Most preferably, the alkalizing agent is selected from the group consisting of the monoalkanolamines, e.g. monoethanolamine, N-methyl,-ethyl, or-propyl ethanolamine, 2-amino-2-methylpropanol, 1-amino-2-propanol, 2-amino-1-propanol, N,N-dialkylaminoethanol and N,N -dialkylaminopropanol; aminoalkyldiols, e.g. 2-amino-2-ethyl-1,3-propanediol; and amino alkyltriols, e.g. 2-amino-2-hydroxymethyl-1,3-propanediol.

The alkalizing agent is generally present in an amount of from about 0.1% to about 30%.

More preferably, it is present in amount of from about 0.5% to about 20%.

Most preferably, it is present in an amount of from about 1% to about 10%.

The presence of a thickening agent is desirable. The thickening agent functions to increase the viscosity of the composition and reduces (and most desirably prevents) running of the composition upon application. Suitable thickening agents include sodium alginate; gum arabic; xanthan gum; cellulose derivatives, e.g. methylcellulose, hydroxyethylcellulose, hydroxypropylmethylcellulose, carboxymethylcellulose; and acrylic acid derived polymers.

More preferably, the thickening agent is selected from the group consisting of gum arabic; xanthan gum and cellulose derivatives, e.g. methylcellulose, hydroxyethylcellulose, hydroxypropylmethylcellulose and carboxymethylcellulose.

Most preferably, the thickening agent is selected from the group consisting of cellulose derivatives, e.g. methylcellulose, hydroxyethylcellulose, hydroxypropylmethylcellulose and carboxymethylcellulose.

Generally, the thickening agent is present in an amount of from about 0.1% to about 10%.

More preferably, it is present in amount of from about 0.5% to about 3%.

Most preferably, it is present in an amount of from about 0.75% to about 2.5%.

The compositions of the present invention can include other direct dyes and/or oxidation dyes. Further, the compositions can also include adjuvants conventionally employed in hair dye compositions, such as wetting agents, emollients, perfumes, antioxidants, sequestering agents and the like.

The composition can be packaged under pressure in aerosol containers with conventional liquified aerosol propellent(s).

The composition is generally applied to keratin fibers, such as human hair, for a period ranging from about 5 to 45 minutes. The hair is then generally rinsed, washed and dried.

What is claimed is:

1. A process for coloring a keratin fiber comprising contacting such fiber with an amount effective to directly dye same of a 4-nitroso aniline of the formula I

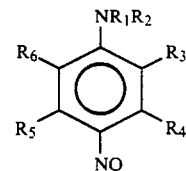

wherein $R_1$ and $R_2$ are the same or different, and are H, $C_1$–$C_6$ alkyl, $C_1$–$C_6$ hydroxyalkyl or polyhydroxyalkyl, $C_1$–$C_6$ alkoxyalkyl or polyalkoxyalkyl, $C_1$–$C_6$ aminoalkyl, $C_1$–$C_6$ dialkylaminoalkyl, or $R_1$ and $R_2$ taken together with the nitrogen atom to which they are attached may be a heterocyclic ring selected from the group consisting of morpholino, pyrrolidino, piperidino and piperazino; $R_3$, $R_4$, $R_5$, and $R_6$ can be the same or different, and are H, $C_1$–$C_6$ alkyl, $C_1$–$C_6$ hydroxyalkyl or polyhydroxyalkyl, hydroxy, $C_1$–$C_6$ alkoxy, $C_1$–$C_6$ hydroxyalkoxy or polyhydroxyalkoxy, or halogen; or a cosmetically acceptable salt thereof; said contacting step being carried out for a sufficient period of time to dye said fiber.

2. The process according to claim 1, wherein the contacting step is carried out at ambient temperature.

3. The process according to claim 1, further including the steps of rinsing, washing and drying the fiber after it is dyed.

4. The process according to claim 1, wherein said contacting step is carried out for a period of time of from about 5 to about 45 minutes.

* * * * *